US007216792B2

(12) United States Patent
Saraf et al.

(10) Patent No.: US 7,216,792 B2
(45) Date of Patent: May 15, 2007

(54) SELF ASSEMBLED NANO-DEVICES USING DNA

(75) Inventors: Ravi F. Saraf, Briar Cliff Manor, NY (US); Hemantha K. Wickramesinghe, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 231 days.

(21) Appl. No.: 10/657,093

(22) Filed: Sep. 9, 2003

(65) Prior Publication Data

US 2004/0046002 A1 Mar. 11, 2004

Related U.S. Application Data

(60) Division of application No. 09/972,958, filed on Oct. 10, 2001, now Pat. No. 6,656,693, which is a continuation of application No. 09/604,680, filed on Jun. 27, 2000, now abandoned, which is a continuation of application No. 09/154,575, filed on Sep. 17, 1998, now abandoned.

(51) Int. Cl.

| | |
|---|---|
| ***A47J 36/02*** | (2006.01) |
| ***B23K 31/02*** | (2006.01) |
| ***B23K 11/00*** | (2006.01) |

(52) U.S. Cl. ............. 228/101; 228/180.21; 219/78.01; 257/E51.023

(58) Field of Classification Search ..................... 435/6
See application file for complete search history.

(56) References Cited

U.S. PATENT DOCUMENTS 5,609,907 A * 3/1997 Natan ........................ 427/2.12

FOREIGN PATENT DOCUMENTS

| | | |
|---|---|---|
| JP | 08 329688 | 12/1996 |
| JP | 10 015857 | 1/1998 |

OTHER PUBLICATIONS

Ralf Landgraf et al., Double-stranded scission of DNA directed through sequence-specific R-loop formation. Nucleic Acids Research, 1995, vol. 23, No. 17, 3524-3530.

* cited by examiner

*Primary Examiner*—Kenneth R. Horlick
*Assistant Examiner*—Cynthia Wilder
(74) *Attorney, Agent, or Firm*—Connolly Bove Lodge & Hutz, LLP; Robert M. Trepp

(57) ABSTRACT

An article of manufacture including an organic structure and inorganic atoms bonded to specific locations on the organic structure.

50 Claims, 4 Drawing Sheets

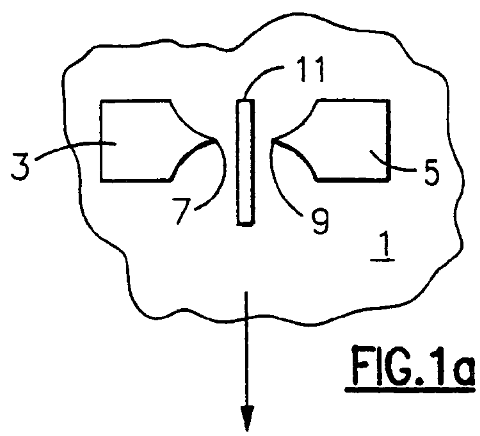
FIG.1a
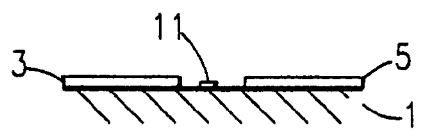
FIG.2
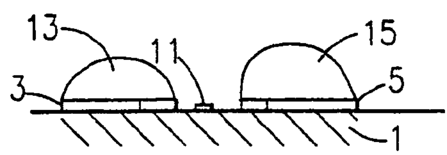
FIG.1b
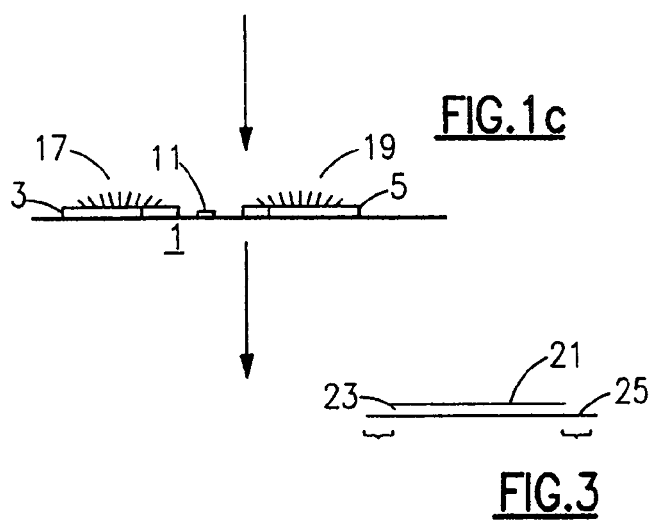
FIG.1c
FIG.3
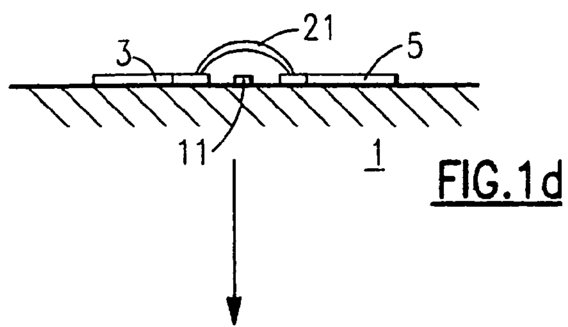
FIG.1d

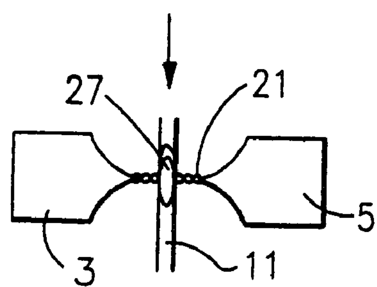
FIG.1e
FIG.4
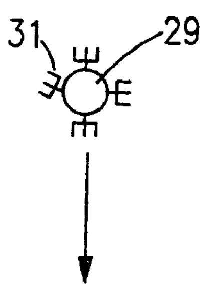
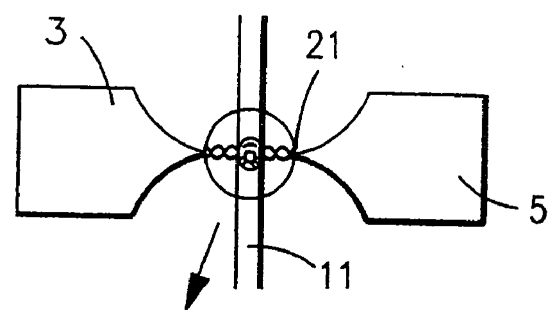
FIG.1f
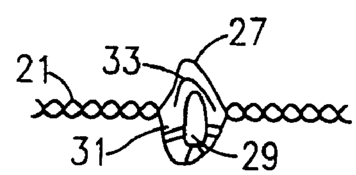
FIG.5

SELF ASSEMBLED NANO-DEVICES USING DNA

CROSS-REFERENCE TO RELATED APPLICATIONS

This application is a division of U.S. patent application Ser. No. 09/972,958 filed Oct. 10, 2001, now issued as U.S. Pat. No. 6,656,693; which was a continuation of U.S. patent application Ser. No. 09/604,680 filed Jun. 27, 2000, abandoned; which was a continuation of U.S. patent application Ser. No. 09/154,575 filed Sep. 17, 1998, abandoned.

FIELD OF THE INVENTION

The present invention relates to the field of semiconductor chips. In particular, the present invention relates to semiconductor chips that include active device having extremely small feature sizes. The present invention also relates to methods for forming semiconductor chips including active features having such sizes.

BACKGROUND OF THE INVENTION

The shrinking dimensions of active devices on silicon chip is approaching its limit due to restrictions set by photolithographic techniques. For example, wave properties of radiation, such as interference and diffraction, can limit device size and density. Considerable research has taken place to overcome the limitations of photolithographic techniques.

The research has been directed at correcting the problems, such as by phase shift lithography as well as to developing other novel approaches. Concomitantly, with this research, there have been developments in device design utilizing electron confinement in small volume. The three basic categories are such devices design are Quantum Dots (QD), Resonant Tunneling Devices (RTD), and Single Electron Transistors (SET). Quantum Dots are discussed in greater detail in R. Turton, The Quantum Dot, Oxford, U.K., Oxford University Press, 1995; Resonant Tunneling Devices are discussed in greater detail in A. C. Seabaugh et al., Future Electron Devices (FED) J., Vol. 3, Suppl. 1, pp. 9-20, (1993); and Single Electron Transistors are discussed in greater detail in M. A. Kastner, Rev. Mod. Phys., Vol. 64, pp. 849-858, (1992); the entire disclosures of all of which is hereby incorporated by reference.

SUMMARY OF THE INVENTION

Aspects of the present invention provide an article of manufacture including an organic structure and inorganic atoms bonded to specific locations on the organic structure.

Other aspects of the present invention includes a structure including a DNA molecule that includes an R-loop. A nanoparticle is bound to the DNA molecule in the interior of the R-loop.

Additional aspects of the present invention provide a structure that includes an electrode positioned by a biomolecule and a nanoparticle spaced apart from the biomolecule.

Further aspects of the present invention provide a method for self assembly of inorganic material utilizing a self assembled organic template. The method includes forming an organic structure and bonding inorganic atoms to specific locations on the organic structure.

Still further aspects of the present invention provide a structure including a substrate, a first electrode and a second electrode on the substrate, and an organic molecule extending between the first electrode and the second electrode. A nanoparticle bonded to the organic molecule.

Also, aspects of the present invention provide a method for forming a structure. The method includes forming a first electrode on a substrate. A second electrode is formed on the substrate. A DNA molecule is extended between the first electrode and the second electrode. At least one nanoparticle is inserted into at least one location in the DNA molecule.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which:

FIGS. 1*a*, 1*e*, and 1*f* represent overhead views and FIGS. 1*b*, 1*c*, and 1*d* represent cross-sectional views of an embodiment of a device according to the present invention at various stages of an embodiment of a process according to the present invention;

FIG. 2 represents a cross-sectional view of a device illustrated in FIG. 1*a;*

FIG. 3 represents an embodiment of an embodiment of a DNA molecule that may be utilized according to the present invention;

FIG. 4 represents an embodiment of a nanoparticle that may be utilized according to the present invention;

FIG. 5 represents an embodiment of an embodiment of a DNA molecule including an R-loop and an embodiment of a nanoparticle that may be utilized according to an embodiment of the present invention;

DETAILED DESCRIPTION OF THE INVENTION

Figure 6:
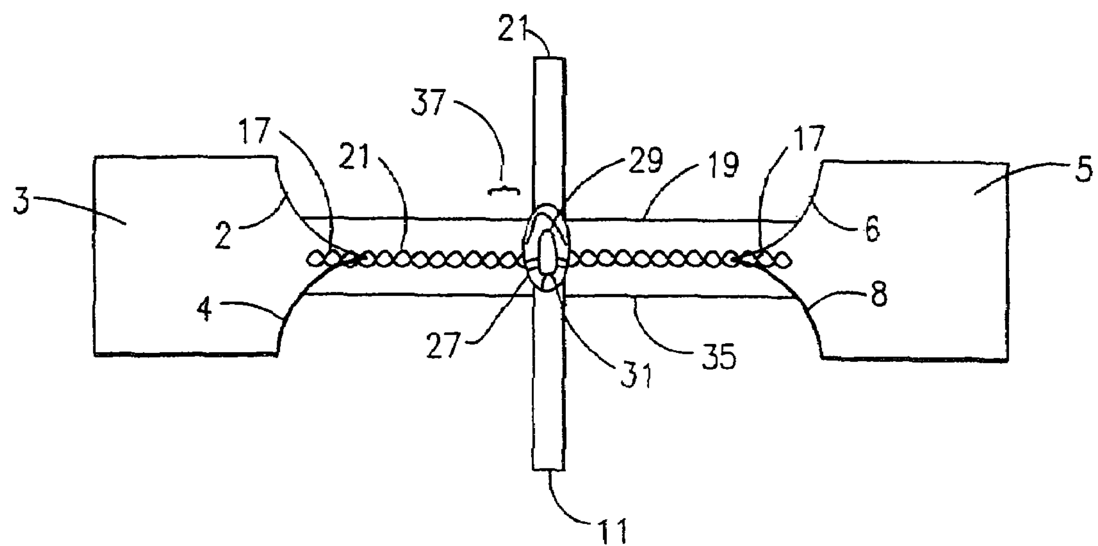
FIG. 6 represents an overhead view of an embodiment of a device according to the present invention.

The present invention provides methods for overcoming and actually circumventing problems associated with photolithographic techniques. The resulting devices are potentially much smaller than those created by the commonly known techniques. Accordingly, the present invention includes a novel fabrication method to make devices on a nanometer scale, or nanodevices. The present invention could be considered to fall under the category of a Resonant Tunneling Device referred to above.

To create such devices, the present invention utilizes the self-organizational nature of some biological molecules. For example, the present invention may make use of nucleic acids and their properties, including their self-organizational nature. In particular, the present invention may utilize both deoxyribonucleic acid (DNA) and ribonucleic acid (RNA) to create the devices.

The nature of DNA and RNA is well known. A few nucleic acid bases are attached together to make up a longer molecule. In the case of DNA, two of these longer molecules are bonded together and form a double helix structure. RNA molecules typically are formed by transcribing one strand of the double stranded DNA during protein synthesis. For background purposes, reference is made to BIOCHEMISTRY, Lubert Stryer, W. H. Freeman and Company, the entire contents of which are hereby incorporated by reference.

A structure according to the present invention typically includes a substrate upon which the nanodevices of the invention may be created upon. The substrate may include a glass. Also, the substrate, whether a glass other form, may include any common semiconductor material. For example, the substrate may include silicon.

Electrodes may be arranged on the substrate. Typically, at least two electrodes are arranged on the substrate. The electrodes may be formed on the substrate according to common photolithographic techniques.

The electrodes may be made of any oxide free, electrically conducting material. For example, the electrodes may be made of any noble metal or alloy that includes noble metal. Preferably, the electrodes are made of an oxide-free metal. According to one example, the electrodes are made of gold.

FIG. 1*a* represents an overhead view of an embodiment of a substrate 1 with two electrodes, a first electrode 3 and a second electrode 5, provided on the surface of the substrate or on other structures formed in and/or on the substrate. The first electrode 3 and second electrode 5 may be provided in close proximity to each other. The distance between the first electrode and the second electrode may vary, depending upon the embodiment. According to one example, the first electrode and the second electrode may be separated by a distance of from about 0.1 μm to about 100 μm. Typically, the electrodes are separated by a distance of from about 1 μm to about 10 μm. Additionally, the electrodes typically have a thickness of about 20 nm to about 1000 nm.

The first electrode and the second electrode may have a variety of shapes, depending upon the embodiment. FIG. 1(*a*) illustrates an example in which the first electrode 3 and the second electrode 5 terminate in points 7 and 9 that face each other. Although the sides of the electrode that 2, 4, 6, and 8 that form the points are curved in the embodiment shown in FIG. 1(*a*), the sides may have any curve, including straight. The configuration of the remaining portion of the first electrode and the second electrode may vary, as long as the remaining portion provides an area for connection of a power source to apply power to the first electrode and the second electrode.

The present invention may include a third electrode 11 on the substrate 1. The third electrode 11 may be referred to as a gate electrode. The function of the third electrode will be discussed below in greater detail.

The third electrode 11 may be positioned between the first electrode 3 and the second electrode 5 as illustrated in the embodiment shown in FIG. 1(*a*). The third electrode 11 may also be formed by utilizing common photolithographic techniques, although other techniques may be utilized.

The configuration, such as the shape, of the third electrode 11 may vary, depending upon the embodiment. For example, the third electrode 11 illustrated in FIG. 1(*a*) is substantially a long, thin rectangle, in other words, substantially a straight line.

The thickness of the third electrode may vary, depending upon the application. For example, the third electrode may have a width of from about 100 nm to about 5000 nm. Preferably, the third electrode is as thin as possible. According to one embodiment, the third electrode has a thickness of less than about 100 nm.

The dimensions, especially the thickness, of the three electrodes, including the third electrode may be controlled by a variety of factors. For example, the dimensions of the electrodes, and especially the third electrode, may be controlled by the quality of the film, such as the noble metal or alloy described above, that the electrodes are made of. Film quality characteristics that may affect dimensions of the third electrode include smoothness, conductivity and adhesion.

The exact location of the third electrode may vary, depending upon the embodiment. For example, the purpose of the third electrode may control its position. According to one embodiment, the third electrode 11 is positioned equidistant from the tips 7 and 9 of the first electrode 3 and the second electrode 5. According to one embodiment, the third electrode may be arranged such that it is perpendicular to a line connecting the points 7 and 9 of the first electrode 3 and the second electrode 5.

As with the first electrode 3 and the second electrode 5, the third electrode 11 may be made of any electrically conducting material. For example, the third electrode may be made of any metal, or alloy. Preferably, the third electrode is made of an oxide-free metal. According to one example, the third electrode is made of gold.

FIG. 2 represents a cross-sectional view of the embodiment of the substrate and the first electrode, the second electrode, and the third electrode shown in FIG. 1*a*.

Figure 8:
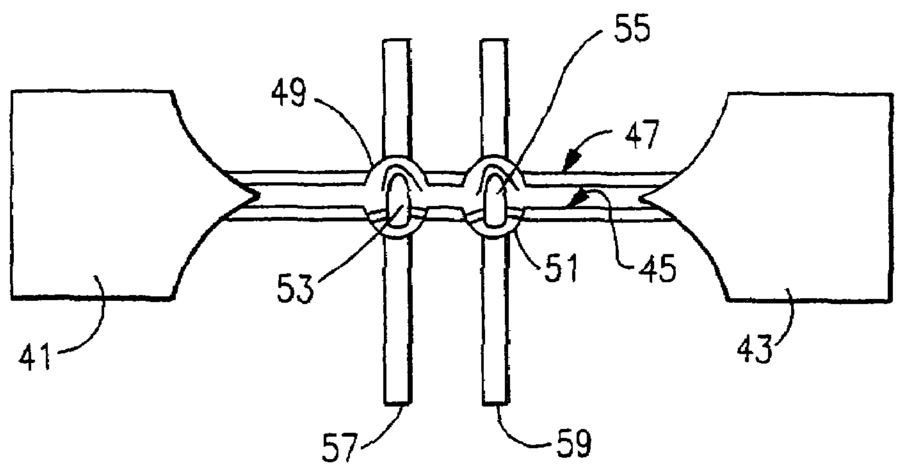
FIG. 8 represents an overhead view of an embodiment of a device according to the present invention that forms an AND gate.

The present invention may also include a fourth electrode positioned between the first electrode 3 and the second electrode 5. FIG. 8 illustrates such an embodiment. The fourth electrode may be substantially similar to the third electrode described above. According to some embodiments, more than one electrode may extend between each pair of electrodes.

Additionally, the present invention may include more than one pair of electrodes such as the first electrode 3 and the second electrode 5. For example, the embodiment of the device illustrated in FIG. 9 includes two pairs of electrodes. Each pair of electrodes in the embodiment shown in FIG. 9 includes an electrode therebetween similar to the electrode 11 between the first electrode 3 and the second electrode 5 in the embodiment shown in FIG. 1*a*.

After provision of the electrodes, whether by photolithographic techniques or otherwise, at least one organic structure may be extended between the first electrode 3 and the second electrode 5, as in the embodiment illustrated in FIG. 1*a*. However, it is not necessary that the organic structure extend between two electrodes. The at least one organic structure may include at least one inorganic atom bonded to at least one specific location. The bonding could be any sort of bonding, whether hydrogen, ionic, covalent or otherwise. The inorganic atoms may be electrically conducting and form an electrical conductor.

The at least one inorganic atom that may be bonded to the organic structure could include a nanoparticle. The nanoparticle may include at least one partially electrically conducting material. For example, the nanoparticle may include at least one material selected from the group consisting of a noble metal or a noble metal alloy. According to one example, the nanoparticle is gold.

The nanoparticle can include a plurality of elements. For example, if the nanoparticle is gold, the gold may be in a ball having a diameter of from about 1 nm to about 100 nm. The particle may be coated with at least one surfactant. The surfactant may have terminal groups x and y. The groups x and y may be arranged at the end of a polymer. For example, the groups x and y may be bonded to the ends of a polymer. The polymer may include a variety of monomers. Examples of the monomers include

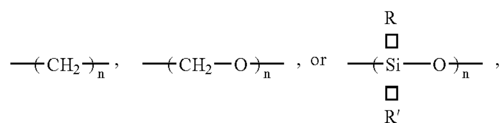

wherein n>1; R and R'$=CH_3$, $C_2H_5$,

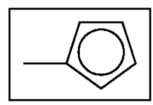

The group x may include —SH. On the other hand, the group y may include

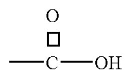

or a nucleotide base.

The x group may bond with the gold or silver, for example, particle. The y group may bond with the nucleotide. If y is an acid group, the acid group may react wit the amine group of the DNA base. If y is a nucleotide base group, the base may hydrogen bond to the DNA molecule.

As stated above, the present invention includes an organic structure. The organic structure may extend between the first electrode 3 and the second electrode 5 as discussed above. The organic structure may include DNA.

The DNA that may be included in the present invention may be single stranded or double stranded. The length of the DNA strand included in the organic structure according to the present invention may be from about 300 to about 300,000 bases, or base pairs in the case of double stranded DNA. Alternatively, the length of the DNA molecule may be about 0.1 ìm to about 100 ìm.

According to one embodiment, the DNA is λ-DNA. However, any DNA molecule having any sequence of bases may be utilized according to the present invention. In other words, the DNA may be subjectively selected.

The DNA molecule that may be included in a structure according to the present invention may include an R-loop. Description of R-loops may be found in Asai and Kogoma, *D-Loops and R-Loops: Alternative Mechanisms for the Initiation of Chromosome Replication in Escherichia coli*, JOURNAL OF BACTERIOLOGY, April 1994, pp. 1807-1812; Landgraf et al., *R-loop stability as a function of RNA structure and size,* NUCLEIC ACIDS RESEARCH, 1995, Vol 23, No. 7, pp. 3516-3523; Landgraf et al., *Double stranded scission of DNA directed through sequence-specific R-loop formation*, NUCLEIC ACIDS RESEARCH, 1995, Vol 23, No. 7, pp. 3524-3530; and Masai and Arai, *Mechanisms of primer RNA synthesis and D-loop/R-loop dependent DNA replication in Escherichia coli*, BIOCHEMIE (1996) 78, pp. 1109-1117, the entire contents of all of which are hereby incorporated by reference.

Figure 9:
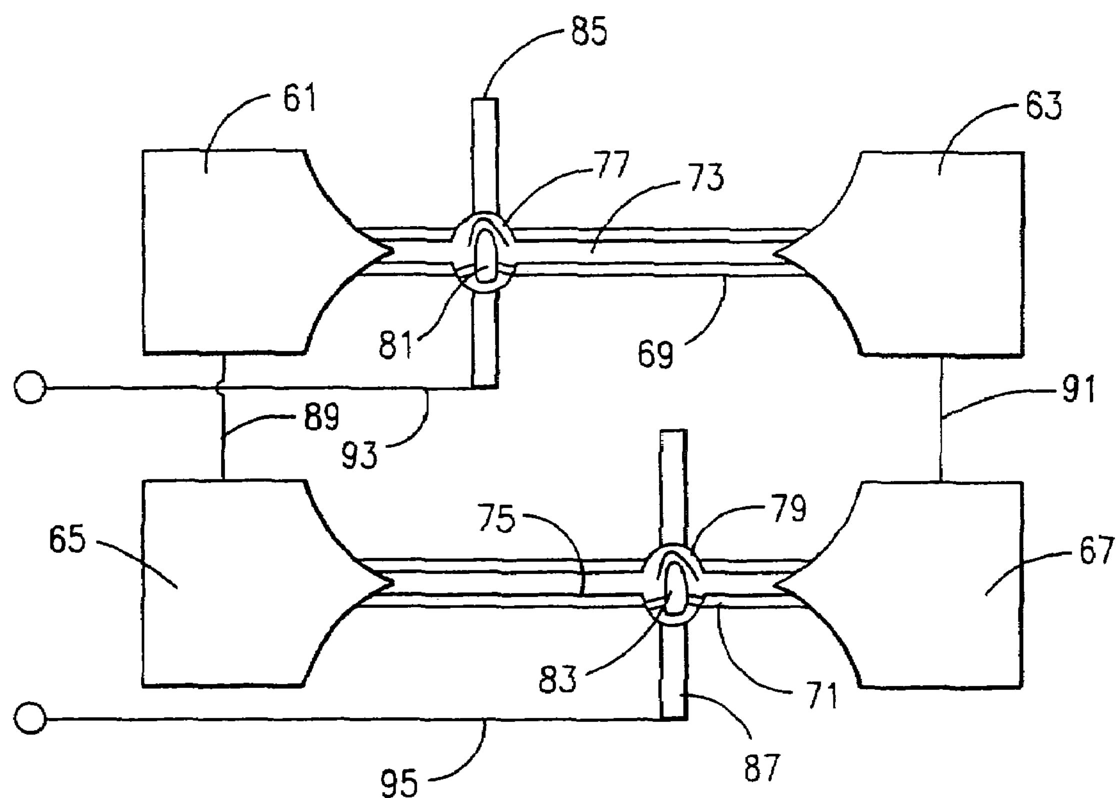
FIG. 9 represents an overhead view of an embodiment of a device according to the present invention that forms an OR gate.

The R-loop may function to provide a site for the attachment of the nanoparticle(s) to the DNA molecule. Accordingly, the DNA molecule may include at least one R-loop. FIG. 9 illustrates an embodiment that includes two R-loops.

Each R-loop may include at least one nanoparticle bonded to a portion of the DNA within the R-loop. In addition to including more than one R-loop, more than one nanoparticle could be attached to a portion of the DNA molecule within each R-loop. Steps for attaching the nanoparticle(s) to the R-loop are discussed below in greater detail.

The R-loops may be formed according to any known technique for forming R-loops, such as those disclosed in the above-references scientific literature articles. At least one RNA molecule having a sequence complementary to at least one portion of the DNA molecule may be utilized in formation of the R-loop. As stated above, the DNA molecule may include more than one R-loop. Therefore, the more than one RNA molecule may be utilized to form R-loops in the DNA molecule. Each RNA molecule may have a sequence complementary to a different sequence of the DNA molecule.

The sequence of the RNA molecule may be controlled to control where the R-loop(s) is(are) created. For example, if the DNA molecule is to include one R-loop and the R-loop is to be centrally located in the DNA molecule, the RNA molecule may have a sequence complementary to a sequence of the DNA molecule such that the RNA molecule will be substantially centered on the DNA molecule, equidistant from the ends of the DNA molecule upon formation of the R-loop. According to another example, such as that shown in FIG. 9, the RNA molecules may have a sequence complementary to sequences of the DNA molecule such that the RNA molecules will be positioned to divide the DNA molecule into three portions having substantially equal lengths upon formation of the R-loop.

The sequence of the RNA molecule that may be utilized in forming the R-loop(s) may vary, depending upon the positioning of the DNA molecule relative to an electrode that may lie under the DNA molecule. Along these lines, the RNA molecule may have a sequence such that the R-loop may be positioned over an underlying electrode. If the present invention includes more than one R-loop and the R-loops each overly an electrode, the RNA molecules utilized in forming the R-loops may have sequences such that the R-loops will be positioned over the underlying electrodes, such as the third electrode 11 in the embodiment illustrated in FIG. 1*a*.

As stated above, the present invention may include at least one nanoparticle. To facilitate bonding of the nanoparticle to the organic structure, the nanoparticle may include one or more atoms or chemical groups attached to the nanoparticle. By attaching one or more such atoms or groups, the nanoparticle may be "functionalized".

In the case where the organic structure includes a DNA molecule, at least one nucleotide may be attached to the nanoparticle. The at least one nucleotide attached to the nanoparticle typically is complementary to at least one nucleotide within the R-loop of the DNA molecule on the portion of the R-loop not attached to the RNA molecule.

Therefore, the nucleotide attached to the nanoparticle may depend upon the sequence of the DNA molecule and where it is desired that the nanoparticle attach to the DNA molecule. The nanoparticle and the attachment of the nanoparticle to the DNA molecule are discussed above in greater detail.

The nanoparticle may attach to the portion of the DNA molecule anywhere within the R-loop. According to one embodiment, the nanoparticle attaches to the DNA about in the center of the portion that lies within the R-loop. Therefore, the location of the R-loop may depend upon the location of the R-loop. For example, the nanoparticle may be attached to the DNA molecule midway between the ends of the DNA molecule if the DNA molecule includes one R-loop substantially in the center of the DNA molecule.

The present invention may include an electrically conducting material on the organic structure. The electrically conducting material may include any electrically conducting material. According to one example, silver may form a salt with the organic structure. Metallic silver may also be provided on the organic structure.

The electrically conducting material on the organic structure provides a conductor on the organic structure. In certain cases, this conductor may be used to form functional structures. An electrically conducting material on the organic structure may provide a capacitive linkage between the electrically conducting material on the organic structure and an underlying electrode. This may be accomplished through the functionalizing atoms and/or groups of atoms on the nanoparticle. The conductor(s) on the organic structure may be utilized in forming logic devices. For example, as described below in greater detail, a structure according to the present invention may be utilized in forming an AND gate and an OR gate, among other structures.

In the case where the organic structure includes DNA, an R-loop in the DNA and a nanoparticle attached to the DNA molecule in the R-loop, the electrically conducting material on the organic structure may provide a conductor to the two sides of the R-loop on the DNA molecule.

The electrically conducting coating may be applied to the organic structure by immersing the organic structure in a solution that includes silver ions. The silver ions in the solution may then form a silver salt with the organic structure. In the case where the organic structure includes DNA, the silver may form a salt with phosphate groups of the DNA molecule.

After formation of a salt, the silver in the salt may be reduced to metallic silver with a reducing agent. Examples of reducing agents that may be utilized include hydroquinone/$OH^-$ followed by hydroquinone/$OH^+$.

The organic structure may be connected to electrodes on the surface of a substrate, such as the first electrode and the second electrode in the embodiment illustrated in FIG. 1*a*. The electrodes are described above in greater detail. The connection may be effected in a variety of ways. For example, the connection may be carried out by providing sites on the electrodes that the organic structure may be attached to.

The attachment sites may be provided by a variety of structure. For example, one or more atoms or molecules may be provided on one or more of the electrodes. According to one example, at least one organic molecule is provided on at least one of the electrodes. The organic molecule could be bonded to the surface of the electrode(s).

According to one example, in which the organic structure includes a DNA molecule extending between the first electrode and the second electrode, at least one DNA and/or RNA molecule may be attached to the first electrode 3 and the second electrode 5 shown in FIG. 1A. In the case where the organic structure includes DNA, typically, DNA is provided on the first electrode and the second electrode. The DNA may be provided on the electrodes in a variety of ways.

According to one example, the DNA is bonded to an atom or molecule that facilitates its connection to the electrodes. For example, the DNA could be sulfur terminated. The sulfur terminated ends could attach to the surface of the gold electrodes. It is well known that $S^-$ terminated compounds bond to a gold surface.

The DNA molecule extending between the first electrode and the second electrode may bond to the DNA and/or RNA on the electrodes. For example, both the DNA molecule that is to extend between the two electrodes and the DNA molecule(s), as in the above example, attached to the electrodes could have a single stranded portion. The single stranded portions on the DNA molecule that is to extend between the first electrode and the second electrode and the DNA molecule(s) attached to the first electrode and the second electrode may have complementary ends to facilitate their bonding to each other.

According to one embodiment, the DNA that is attached to the electrodes is single stranded, sulfur terminated DNA. Regardless of whether single or double stranded DNA or RNA is bonded to the electrodes, the DNA and/or RNA may include from about 5 to about 20 bases. However, the DNA and/or RNA molecules could be as long as about 100 bases. For example, the DNA and/or RNA molecules could be about 15 to about 30 bases. However, the DNA and/or may be as short or as long as necessary to ensure that the DNA and/or functions to attach to the first electrode and the second electrode the DNA and/or that is to extend between the first electrode and the second electrode.

Additionally, regardless of whether single or double stranded DNA or RNA molecules are bonded to the electrodes, the DNA and/or RNA molecules attached to one electrode may have a different sequence of bases than the DNA and/or RNA molecules attached to the other of the electrodes. Alternatively, a portion of the DNA and/or RNA molecules that the DNA that is to extend between the first electrode and the second electrode may have a different sequence, rather than the entire DNA and/or RNA molecules.

According to an embodiment in which DNA molecules are attached to the electrodes and the DNA molecules include a sequence of bases to bond to the DNA molecule that is to extend from between the first electrode and the second electrode, the DNA molecule that is to extend between the first electrode and the second electrode may include "sticky ends" that have a sequence of bases that is complementary to the DNA attached to the first electrode and the second electrode.

FIG. 3 illustrates an embodiment of a DNA molecule 21 that is to extend between the first electrode and the second electrode. The DNA molecule 21 is shown in a linear configuration. The sticky ends 23 and 25 are provided on the ends of the DNA molecule.

After constructing or otherwise obtaining the DNA molecules to be attached to the first electrode and the second electrode they may be attached to the electrodes. A solution may be formed, that the DNA molecules are to be added to. First, an aqueous solution of a salt is formed. One Example of a salt is sodium chloride. Each DNA molecule, where a different molecule is to be attached to each electrode, may then be added to the solutions.

After formation of the solutions, a quantity 13 of one solution may be placed on the first electrode 3 and a quantity 15 of the other solution may be placed on the second electrode 5. Which solution is placed on which electrode may depend upon how it is desired that the DNA molecule that is to extend between the first electrode and the second electrode is to be oriented. The quantity of the solution deposited on each electrode may depend upon the concentration of the DNA, RNA, and/or other molecule that is in the solutions.

In determining the above factors, the resulting final structure is important. That is, one DNA bridge from electrode 3 to electrode 5 should form. The concentration of volume typically is secondary. A flowing solution could also be utilized.

After application of solutions to the first electrode and the second electrode to deposit the desired molecules on the electrodes, the solutions may be removed. Typically, the solutions are permitted to remain on the electrodes for a time sufficient for a number of molecule to be attached to the electrodes to facilitate the attachment of the organic structure between the two electrodes. Typically, the solutions remain for a time of about 10 minutes to about 20 minutes.

Removal of the solution may be carried out in a number of ways. For example, the solution may be washed off. For example, water could be utilized to wash the solution off. Typically, the solution is washed off with a liquid that does not include any moieties that attach to —S—Au bonds. Alternatively, the solution could be permitted to dry with our without the application of heat. According to one example., an air gun could be utilized.

FIG. 1*c* illustrates the first electrode 3 and the second electrode 5 once the solution has been removed. The molecules 17 and 19 remain attached to the first electrode and the second electrode.

After attachment of the anchoring molecules to the electrodes, the structure that is to extend between the first electrode and the second electrode may be applied to the structure, such as illustrated in FIG. 1*c*. In the case where the organic structure includes DNA, the DNA may be applied to the substrate over the electrodes and space between the electrodes. The organic structure could be applied in a solution. One method for creating a DNA bridge between electrodes is disclosed in Braun et al., *DNA-templated assembly and electrode attachment of a conducting silver wire,* Nature, Vol. 391, pp. 775-777, Feb. 19, 1998, the entire contents of which is hereby incorporated by reference.

After application of the DNA molecule(s), the ones that are to extend between the first electrode and the second electrode, to the substrate and electrodes they may bond to an organic structure, such as anchoring molecules, attached to the electrodes. To promote a desired orientation of the DNA molecules with respect to the electrodes and anchoring molecules, such as the DNA described above, the DNA that is to extend between the first electrode and the second electrode may be subjected to conditions that tend to align them. The conditions could include subjecting the DNA molecules to an E-field or a flow field. If an E-field is utilized, it may be from about $10^4$ to about $10^6$ V/cm. On the other hand, if a flow field is utilized, V may be from about 1 to about 100 cm/sec.

Encouraging the DNA to align in a particular manner helps to ensure that at least one of the DNA molecules will extend between the first electrode and the second electrode. Typically, how only "DNA bridge" is formed between the electrodes. Additionally, typically, no DNA bridges will extend outside of the region where the DNA bridge is shown in FIG. 1*d*.

To facilitate formation of the DNA bridge(s), a fluorescent dye may be utilized to tag the DNA. The experiment is done under a microscope. As soon as one bridge is formed, the solution containing the DNA may be purged from the area of the electrodes.

After bonding of the DNA molecule(s) to the first electrode and the second electrode, at least one R-loop may be formed in each DNA molecule that forms a "bridge" between the first electrode and the second electrode. Typically, the R-loop is formed in a region of the DNA molecules between the first electrode and the second electrode that is arranged over another electrode, such as the third electrode described above. The formation of the R-loop is described above. FIG. 1*e* illustrates a DNA molecule 21 extending between the first electrode and the second electrode, wherein the DNA molecule includes one R-loop 27 in the region of the DNA molecule over the third electrode 11.

After formation of the R-loop(s), a nanoparticle 29 may be bonded to the DNA molecule. The nanoparticle may be bonded to a portion of the DNA molecule that lies within the R-loop and is not attached to the RNA molecule. To accomplish attachment of the nanoparticle to the DNA molecule, a suspension of the nanoparticle may be formed. The suspension may include nanoparticles with a modified surface, as described above. The nanoparticles may be suspended in water at a concentration of about 0.1% to about 10%.

After formation of the solution it may be dispensed in a region over the R-loop. The "functionalizing" nucleotides 31 and/or atoms and/or molecules attached to the nanoparticle 29 may then bond to the DNA within the R-loop. FIG. 4 illustrates a nanoparticle 29 with attached nucleotides 31. In the embodiment illustrated in FIG. 4, four nucleotides are attached to the nanoparticle. Typically, about 1 to about 10000 nucleotides attach to the nanoparticle. The nucleotide(s) attached to the nanoparticle may be complementary to one or more nucleotides within the R-loop as described in greater detail above.

In the case of nucleotides on a nanoparticle bonding to a DNA molecule, the nucleotides on the nanoparticle may hydrogen bond to the nucleotides of the DNA molecule(s).

FIG. 1*f* illustrates a DNA molecule extending between a first electrode 3 and a second electrode 5, wherein the DNA molecule includes one R-loop with one nanoparticle bonded to the DNA molecule within the R-loop. FIG. 5 illustrates a close-up view of an embodiment of the DNA molecule, in its double helix configuration, with the R-loop 27, attached RNA 33, nanoparticle 29, and nucleotides 31 attached to the nanoparticle.

After attachment of the nanoparticle(s) to the DNA molecule extending between the first electrode and the second electrode, an electrically conducting material may be provided on the DNA molecule. One example of the deposition of silver is described above. When depositing silver on the DNA molecule that extends between the first electrode and the second electrode, no significant seeding and deposition of silver may take place on the R-loop, due to a lower density of silver ions.

The $Ag^+$ ions form a salt with a phosphate ion in the DNA backbone. In the double helix, the $O^-$ of the phosphate ions are evenly distributed around the double helix. However, the density is about 50% lower in the strand forming R-loop. Also, due to thermal vibration, as the Ag ion is reduced to Ag on the R-loop, it will migrate to the high density region, that is, the double helix region.

FIG. 6 illustrates an overhead view of an embodiment of the present invention after plating of an electrically conducting material 35 on a DNA molecule 21 extending between a first electrode 3 and a second electrode 5 by bonding to DNA molecules 17 and 19 attached to the first electrode and the second electrode. The DNA molecule includes one R-loop 27 with a nanoparticle 29 bonded thereto with at least one nucleotide 31. The structure shown in FIG. 6 results in a capacitive linkage 37 between electrically conducting material 35 on the DNA molecule 21 and the nanoparticle.

Figure 7:
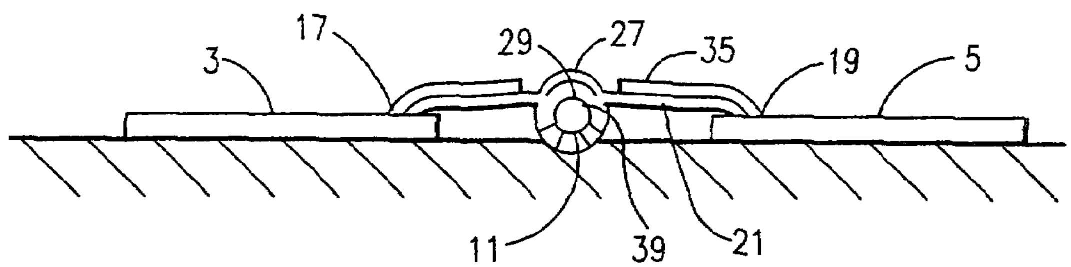
FIG. 7 represents a cross-sectional view of the embodiment of a device illustrated in FIG. 6.

FIG. 7 illustrates a cross-sectional view of the embodiment illustrated in FIG. 6. As can be seen in FIG. 7, the structure illustrated therein also results in formation of a capacitive linkage 39 between the nanoparticle and the electrode 11, which may be considered a gate electrode.

By manipulating the number of electrodes, DNA molecules extending between electrodes, R-loops, nanoparticles, and/or interconnections among the electrodes, nanoparticles, and/or electrically conducting material arranged on the DNA molecules extending between electrodes, various types of devices may be created with structures according to the present invention. The conditions within the structures of the present invention may also be manipulated to create certain effects. For example, at a given bias, current in the electrically conducting material on the DNA molecule that extends between the first electrode and the second electrode may be controlled by regulating a charge in the nanoparticle. This may be done as in a typical Resonant Tunneling Device referred to above and described in detail by Seabaugh et al., referred to and incorporated by reference above.

Along these lines, FIG. 8 illustrates an embodiment of the present invention that includes two electrodes 41 and 43 similar to electrodes 3 and 5 in the embodiment shown in FIGS. 1*a*-1*f*. The embodiment depicted in FIG. 8 also includes an organic structure that includes at least one DNA molecule 45 extending between electrodes 41 and 43. An electrically conducting material 47 is arranged on the DNA molecule. The DNA molecule includes two R-loops 49 and 51, each including one nanoparticle 53 and 55 bound thereto. Furthermore, the embodiment portrayed in FIG. 8 includes two electrodes 57 and 59, similar to electrode 11 in the embodiment illustrated in FIGS. 1*a*-1*f*, acting as gate electrodes, arranged under the R-loops 49 and 51 and the associated nanoparticles 53 and 55. The structure illustrated in FIG. 8 may form an AND gate.

According to another alternative, the present invention could include a structure such as that illustrated in FIG. 9. FIG. 9 shows an embodiment of the present invention that basically includes two embodiments such as the one shown in FIGS. 1*a*-1*f*. Accordingly, the embodiment of the present invention depicted in FIG. 9 includes two pairs of electrodes 61 and 63 and 65 and 67. The embodiment portrayed in FIG. 9 also includes a pair of organic structures that each includes at least one DNA molecule 69 and 71 extending between electrodes 61 and 63 and electrodes 65 and 67, respectively. An electrically conducting material 73 and 75 is arranged on the DNA molecules 69 and 71, respectively. The DNA molecules each include one R-loop 77 and 79, each R-loop including one nanoparticle 81 and 83, respectively, bound thereto. Furthermore, the embodiment portrayed in FIG. 9 includes an electrode 85 and 87, similar to electrode 11 in the embodiment illustrated in FIGS. 1*a*-1*f*, acting as gate electrodes, arranged under the R-loops 77 and 79 and the associated nanoparticles 81 and 83.

The structure illustrated in FIG. 9 may form an OR gate. This may be accomplished by providing an electrical connection 89 between electrodes 61 and 65, an electrical connection 91 between electrodes 63 and 67, and electrical connections 93 and 95 to gate electrodes 85 and 87, respectively.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A method of fabricating an electronic device using biomolecules comprising:

forming first and second electrodes on a substrate;

extending bridging DNA between said first and second electrodes;

providing at least one RNA complementary to a region of said bridging DNA wherein said at least one RNA and said bridging DNA bond to form at least one R-loop; and bonding at least one nanoparticle to said DNA within said at least one R-loop.

2. The method according to claim 1, further comprising arranging an electrically conducting material on said bridging DNA.

3. The method according to claim 1, further comprising arranging a first linker nucleic acid on said first electrode and a second linker nucleic acid on said second electrode.

4. The method according to claim 3, wherein:

said first and second linker nucleic acid are single-stranded, sulfur-terminated, and include from about five to about twenty bases, and said first linker nucleic acid has a first sequence and said second linker nucleic acid has a second sequence different if from said first sequence; and said bridging DNA comprises a first sticky end having a sequence complementary to and hybridizing with said first linker nucleic acid and a second sticky end complementary to and hybridizing with said second linker nucleic acid.

5. The method according to claim 4, further comprising attaching said first linker to said first electrode and said second linker to the second electrode; and hybridizing said first sticky end to said first linker and said second sticky end to said second linker.

6. The method according to claim 4, wherein arranging a first linker nucleic acid on said first electrode and a second linker nucleic acid on said second electrode comprises:

contacting said first electrode with a solution of said first linker;

contacting said second electrode with a solution of said second linker;

bonding said sulfur-termination to said electrode; and rinsing said solutions from said electrodes.

7. The method according to claim 6, further comprising:
contacting a region of the substrate between said first and second electrodes with a solution of said bridging DNA; and
aligning said bridging DNA from said first electrode to said second electrode.

8. The method according to claim 7, wherein the DNA molecule is aligned by inducing an electric field of a flow field between the two electrodes.

9. The method according to claim 8, further comprising:
contacting said bridging DNA with a molecule of RNA, wherein said RNA is complementary to a portion of said DNA;
forming an R-loop in said DNA, wherein the DNA in said R-loop includes at least one region pair-bonded with said RNA and at least one non-bonding region free of pair-bonds; and
attaching a nanoparticle to said non-bonding region.

10. The method according to claim 9, further comprising the step of:
functionalizing the nanoparticle with at least one nucleotide complementary to at least one base of the portion of the DNA loop within the R-loop prior to attaching it to the DNA within the R-loop.

11. The method according to claim 10, further comprising the step of:
forming a suspension of the nanoparticle and dispensing the suspension of the nanoparticle on the DNA molecule extending between the first electrode and the second electrode.

12. The method according to claim 11, further comprising:
depositing an electrically conducting material on said bridging DNA.

13. The method according to claim 11, wherein depositing electrically conductive material on said bridging DNA comprises:
immersing said substrate in a silver-containing solution thereby forming silver salts with phosphate groups of said bridging DNA; and
reducing said silver salts to metallic silver.

14. The method according to claim 13, wherein reduction of the silver salt comprises the steps of: exposing the silver salt to a reducing agent.

15. The method according to claim 14, wherein reduction of the silver salt comprises the steps of: exposing the silver salt to hydroquinone/$OH^-$ followed by hydroquinone/$H^+$.

16. The method according to claim 2, further comprising the step of:
providing a third electrode on the substrate between the first electrode and the second electrode.

17. The method according to claim 16, further comprising:
forming capacitive linkages between the electrically conducting material on said bridging DNA and the third electrode.

18. The method according to claim 16, further comprising:
electrically connecting the electrically conducting material on said bridging DNA to said third electrode to form an OR gate.

19. The method according to claim 2, further comprising:
providing a third electrode and a fourth electrode on the substrate;
extending a second bridging DNA between the third electrode and the fourth electrode, and
bonding at least one nanoparticle to said second bridging DNA.

20. The method according to claim 19, further comprising the step of:
electrically connecting the organic molecules and the electrodes to form an OR gate.

21. The method according to claim 19, further comprising the step of:
electrically connecting one of the first electrode and the second electrode to one of the third electrode and the fourth electrode; and electrically connecting the other of the first electrode and the second electrode to the other of the third electrode and the fourth electrode.

22. The method according to claim 1, wherein a plurality of nanoparticles are bonded at a plurality of locations on said bridging DNA.

23. The method according to claim 1 wherein said first and second electrodes comprise gold.

24. The method according to claim 1 wherein said bridging DNA is double stranded.

25. The method according to claim 1 wherein said bridging DNA is λ-DNA.

26. The method according to claim 1 wherein at least one nucleotide is attached to said nanoparticle.

27. The method according to claim 26 wherein said at least one nucleotide is complementary to at least one nucleotide of said bridging DNA molecule within said R-loop.

28. The method according to claim 26 wherein said at least one nucleotide is complementary to at least one nucleotide of the DNA molecule within the R-loop at a location equidistant from the first electrode and the second electrode.

29. The method according to claim 3 wherein said first and second linker nucleic acids are selected from the group consisting of RNA and DNA.

30. The method according to claim 3 wherein said first and second linker nucleic acids are sulfur terminated and single stranded.

31. The method according to claim 3 wherein said first linker nucleic acid has a different sequence than said second linker nucleic acid.

32. The method according to claim 3 wherein each of said linker nucleic acids consists of from about five to about 100 base pairs.

33. The method according to claim 19 wherein said third electrode has a width of about 100 nm to about 5000 nm.

34. The method according to claim 19 wherein said third electrode has a width of less than 100 nm.

35. The method according to claim 19 wherein said third electrode is perpendicular to said bridging DNA.

36. The method according to claim 19 wherein said bridging DNA contacts said third electrode.

37. The method according to claim 1 wherein said first and second electrodes are separated by a distance of about 1 μm to about 100 μm.

38. The method according to claim 1 wherein the first electrode and the second electrode are made of an oxide-free material.

39. The method according to claim 1 wherein the first electrode and the second electrode terminate in sharp tips that face each other.

40. The method according to claim 1 wherein the substrate comprises a glass.

41. The method according to claim 19, wherein said fourth electrode is positioned between the first electrode and the second electrode.

42. The method according to claim 41 wherein the fourth electrode has a width of about 100 nm to about 5000 nm.

43. The method according to claim 41 wherein the fourth electrode has a width of less than 100 nm.

44. The method according to claim 41 wherein the fourth electrode is perpendicular to said bridging DNA.

45. The method according to claim 41 wherein said bridging DNA contacts the third electrode and the fourth electrode.

46. The method according to claim 16, further comprising electrically connecting the electrically conducting material on said bridging DNA to said third electrode to form an AND gate.

47. The method according to claim 19 further comprising:

providing a fifth electrode on the substrate arranged at least between the first electrode and the second electrode; and providing a sixth electrode on the substrate arranged at least between the third electrode and the fourth electrode.

48. The method according to claim 47 wherein said bridging DNA contact the fifth electrode and the sixth electrode; and the electrodes and the DNA molecules are electrically connected together to form an OR gate.

49. The method according to claim 47, wherein one of the first electrode and the second electrode is electrically connected to one of the third electrode and the fourth electrode and the other of the first electrode and the second electrode is electrically connected to the other of the third electrode and the fourth electrode.

50. The method according to claim 1 further comprising: a plurality of nanoparticles bonded to the bridging DNA.

* * * * *